(12) United States Patent
Harrington et al.

(10) Patent No.: US 8,899,235 B2
(45) Date of Patent: Dec. 2, 2014

(54) TRACHEAL TUBE CONNECTOR DEVICES AND METHODS

(75) Inventors: Roger Harrington, Athlone (IE); Paul Waldron, Galway (IE); James Stephenson, Galway (IE); Seamus Maguire, Athlone (IE)

(73) Assignee: Covidien LP, Mansfield, MA (US)

( * ) Notice: Subject to any disclaimer, the term of this patent is extended or adjusted under 35 U.S.C. 154(b) by 374 days.

(21) Appl. No.: 13/043,775

(22) Filed: Mar. 9, 2011

(65) Prior Publication Data

US 2012/0227746 A1 Sep. 13, 2012

(51) Int. Cl.
*A61M 16/04* (2006.01)
*A61M 16/08* (2006.01)
*B29C 57/02* (2006.01)
A61M 16/00 (2006.01)
A62B 9/06 (2006.01)
B29C 65/00 (2006.01)
B29L 23/00 (2006.01)
B29C 65/48 (2006.01)

(52) U.S. Cl.
CPC ............... *A61M 16/04* (2013.01); *B29C 66/71* (2013.01); *B29L 2023/007* (2013.01); *B29C 65/4895* (2013.01); *B29C 66/7392* (2013.01); A61M 16/0434 (2013.01); *A61M 16/0497* (2013.01); *A61M 16/0816* (2013.01); A61M 2207/00 (2013.01); B29C 66/73151 (2013.01); B29C 66/5344 (2013.01); *B29C 57/02* (2013.01); B29C 65/48 (2013.01)
USPC ..................................................... 128/207.14

(58) Field of Classification Search
USPC ............. 128/207.14, 207.29, 202.27, 204.18, 128/207.15, 207.17, 200.26; 604/96.01–109, 533, 164.1, 164.11, 604/166.01, 167.06; 29/428; 156/60; 403/1, 403/329, 397, DIG. 14
See application file for complete search history.

(56) References Cited

U.S. PATENT DOCUMENTS

| 4,270,778 | A |   | 6/1981  | Brownell |            |
|-----------|---|---|---------|----------|------------|
| 4,834,087 | A | * | 5/1989  | Coleman et al. | 128/207.14 |
| 4,909,248 | A |   | 3/1990  | Mclennan |            |
| 5,052,386 | A | * | 10/1991 | Fischer, Jr. | 128/207.15 |

(Continued)

FOREIGN PATENT DOCUMENTS

WO    2008046418 A1    4/2008

OTHER PUBLICATIONS

Tracoe medical GmbH-Products: Twist; Apr. 1, 2010; 34 pgs.

*Primary Examiner* — Jackie T Ho
*Assistant Examiner* — Mark Wardas
(74) *Attorney, Agent, or Firm* — Fletcher Yoder PC (57) ABSTRACT

Various embodiments of tracheostomy tube assemblies including a cannula, a cap, and a flange are provided. The cannula includes a distal end and a proximal end, the distal end being adapted to be inserted into a patient's trachea. The annular cap includes an annular body having a first surface adapted to be received into the proximal end of the cannula to retain a portion of the cap in the annular body. The flange member includes a second surface that engages the proximal end of the cannula such that the proximal end of the cannula is retained between the second surface of the flange member and the first surface of the annular cap. The flange member also includes a third surface adapted to engage an inner surface of the annular body of the annular cap to retain the flange member between the annular cap and the proximal end of the cannula.

20 Claims, 6 Drawing Sheets

(56) References Cited

U.S. PATENT DOCUMENTS

| | | | | |
|---|---|---|---|---|
| 5,257,620 A | * | 11/1993 | Schermerhorn | 128/200.26 |
| 5,423,776 A | * | 6/1995 | Haindl | 604/533 |
| 5,806,515 A | * | 9/1998 | Bare et al. | 128/207.15 |
| 7,086,402 B2 | | 8/2006 | Peterson | |
| 7,448,387 B2 | | 11/2008 | Janatpour | |
| 8,151,798 B2 | * | 4/2012 | Thomas et al. | 128/207.29 |
| 2003/0197372 A1 | * | 10/2003 | Hoff et al. | 285/256 |
| 2006/0033331 A1 | | 2/2006 | Ziman | |
| 2006/0033334 A1 | | 2/2006 | Weber et al. | |
| 2007/0083262 A1 | | 4/2007 | Matlock | |
| 2007/0255258 A1 | * | 11/2007 | Matlock et al. | 604/535 |
| 2008/0216830 A1 | | 9/2008 | Richards et al. | |
| 2009/0102192 A1 | | 4/2009 | Ziman | |
| 2009/0229614 A1 | | 9/2009 | Bateman | |
| 2009/0241963 A1 | | 10/2009 | MacMillan | |
| 2010/0108076 A1 | | 5/2010 | Chang | |
| 2010/0241073 A1 | | 9/2010 | Anderson et al. | |
| 2010/0307488 A1 | | 12/2010 | Poulsen et al. | |
| 2010/0319705 A1 | * | 12/2010 | Thomas et al. | 128/207.29 |
| 2012/0103341 A1 | * | 5/2012 | Behlmaier | 128/207.14 |

* cited by examiner

TRACHEAL TUBE CONNECTOR DEVICES AND METHODS

BACKGROUND

The present disclosure relates generally to medical devices and, more particularly, to airway devices, such as tracheostomy tubes.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, medical devices, such as tracheal tubes, may be used to control the flow of air and medicaments into or out of a patient airway. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

More specifically, tracheal tubes may be used to control the flow of air or other gases through a patient's trachea. Such tracheal tubes may include endotracheal tubes or tracheostomy tubes. While patients may be intubated using endotracheal tubes during emergencies or shorter hospital stays, tracheostomy tubes are typically used for prolonged ventilation, as the use of a tracheostomy tube may be more comfortable for a patient.

A typical tracheostomy tube is generally inserted into the trachea via a surgical incision in the neck. After insertion of the tube into the trachea, a portion of the tracheostomy tube remains outside the patient. This portion extends outwards from the neck and may connect the tracheostomy tube to a ventilator or other medical device. A stable attachment of the tracheostomy tube to the desired external device is desirable since such a connection may be instrumental in proper patient ventilation. Current designs for tracheal tubes may allow for easy connection to a connector associated with a desired external device but may have various complex structures for conveying air between the connector and the cannula extending into the patient. In some cases, difficulties may exist in the mounting of the cannula in such devices, which must interface with the connector portion of the external device to provide the desired airflow path. Accordingly, there exists a need for tracheostomy tubes that enable proper patient ventilation without the drawbacks associated with current designs.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, provided herein are a flange, a cannula, and a cap that are configured to be coupled together to provide embodiments of a unitary tracheostomy tube assembly. The tracheostomy tube assemblies may be disposable or reusable, and may be capable of conveying gas to and from the patient, such as during medical situations that necessitate prolonged ventilation. As such, the devices and techniques provided herein may enable maintenance of a bidirectional gas flow between the patient and an external ventilation device. Accordingly, the tracheostomy tube assemblies provided herein may be adapted to be inserted into the trachea via a surgical incision in the neck such that after insertion of the tube into the trachea, a portion of tube remains outside the patient. This portion extends outwards from the neck and may connect the tracheostomy tube to a ventilator or other medical device. That is, the provided tracheostomy tube assemblies may be used in conjunction with auxiliary devices, such as airway accessories, ventilators, humidifiers, and so forth, which may cooperate with the tube assemblies to maintain airflow to and from the lungs of the patient. To that end, the cap of the tracheostomy tube assembly may be configured as a connector suitable for attachment to an artificial ventilation system. For example, the cap may be manufactured with an outer diameter dimension of approximately 15 mm to conform to ISO standard dimensions of mating connectors.

Figure 1:
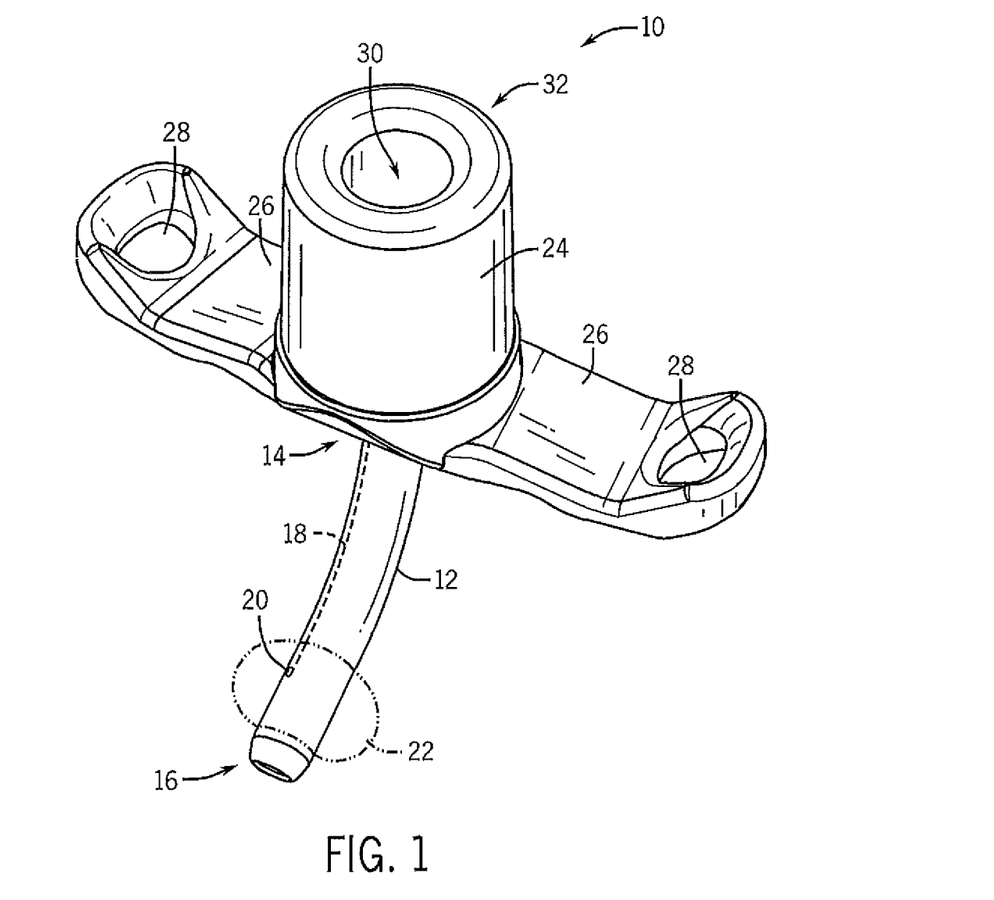
FIG. 1 is a perspective view of a tracheostomy tube assembly including an assembled cap, flange, and cannula according to an exemplary embodiment.

Turning now to the drawings, FIG. 1 is a perspective view of an exemplary tracheal tube assembly 10 according to a presently contemplated embodiment. In the illustrated embodiment, the tracheal tube assembly is designed as a tracheostomy tube assembly, although the present assembly techniques could be used in other tubes, such as endotracheal tubes. In the depicted embodiment, the tracheostomy tube assembly 10 includes an arcuate cannula 12 having a proximal end 14 and a distal end 16, which is generally sized and configured to be inserted into a patient's neck through a surgical incision for prolonged ventilation. For example, in certain embodiments, to conform more aptly to the patient anatomy, a curved section may be provided in the cannula 12 as shown in FIG. 1. When the tracheostomy tube assembly 10 is in use, the distal end 16 as well as the major portion of the length of the cannula 12 will reside within the trachea, with the proximal end 14 being generally flush with the anterior surface of the patient's neck.

In some embodiments, the cannula 12 may also feature a small lumen 18 within the wall, terminating in a notch 20 that may be used to fill a balloon type sealing cuff 22 at the patient insertion end. In some embodiments, the cuff 22 may be a urethane balloon bonded to the exterior of the cannula 12 such that the notch 20 is encompassed. In such embodiments, the cuff 22 may be inflated within the patient's airway to provide an additional seal. To that end, the cuff 22 may be connected to a cuff inflator valve configured to deliver a gas, such as air, through the inflation lumen 18 and into the cuff 22. The cuff 24, when inflated, will expand radially around the cannula 12 to seal the patient's airway. By using one or more cuffs 22 to seal the patient's airway, substances may flow only through the cannula 12, which may allow improved control over the type and amount of substances flowing into and out of the patient as compared to tube assemblies without one or more cuffs.

In some embodiments, the cannula 12 may also include a suction lumen (not shown in FIG. 1) that extends from a location on the proximal end 14 of the cannula 12 positioned outside the body when in use to a location around the cuff 22 inside the body. The suction lumen may terminate in a port through which secretions accumulated around the cuff may be aspirated. For example, a port may be located above the cuff 22 or one or more ports may be located anywhere along the length of the cannula 12 such that their placement facilitates aspiration of secretions from the airway of the patient. Further, in some embodiments, an exterior suction tube may connect to the suction lumen for the removal of the suctioned fluids, for example, via a vacuum connected to the exterior suction tube.

In the illustrated embodiment, the tracheostomy tube 10 further includes a cap 24 that is substantially in line with the proximal end 14 of the cannula 12. The cap 24 may be adapted to directly or indirectly connect the tracheostomy tube assembly 10 to any suitable medical device. For example, in dual cannula tracheostomy tubes, the collar 24 may serve as an insertion point for a disposable cannula lining or may be suitably sized and shaped to connect the tracheostomy tube assembly 10 via medical tubing, suitable connectors, or other devices to a mechanical ventilator. Various sizes of connections to such auxiliary devices are available, and the cap 24 may be dimensioned to accommodate any one of these sizes. For example, in certain embodiments, the cap 24 may have an outer diameter of approximately 15 mm to conform to ISO standard dimensions of mating connectors.

Side flanges 26 extend from the cap 24 for facilitating securement of the tracheosotomy tube assembly 10 to a patient. In the case of the tracheostomy tube shown, the flanges 26 terminate in apertures 28 through which straps or other attachment devices may be inserted to secure the tracheostomy tube assembly 10 to the patient's neck. It should be noted that certain arrangements that incorporate the present teachings, such as endotracheal tubes, may not be provided with flanges.

When the tracheostomy tube assembly 10 is in use, portions of the cannula 12 and the flange 26 are retained within the body of the cap 24 to provide a unitary or integral assembly 10. That is, in embodiments disclosed herein, one or more features of the cap 24 may facilitate the integration of the cannula 12, the flange 26, and the cap 24 into a single assembly, as described in more detail below. As such, when assembled, an air passageway 30 is formed through the cap 24 and extends through the cannula 12 such that, when coupled to appropriate ventilation devices, air or other gasses may be freely exchanged between a proximate end 32 of the cap 24 and the distal end 16 of the cannula 12.

Figure 2:
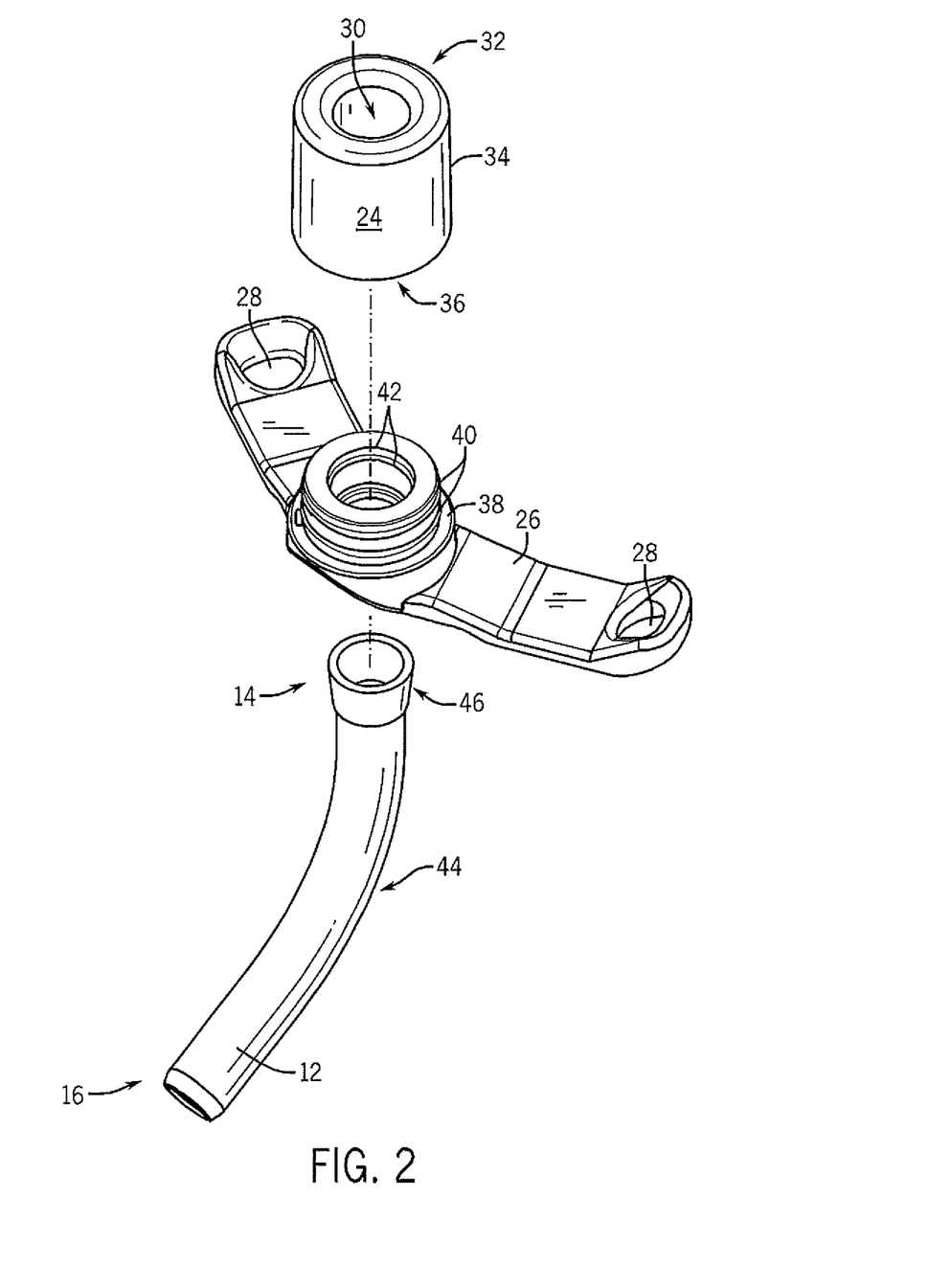
FIG. 2 is an exploded view of the tracheostomy tube assembly of FIG. 1.

FIG. 2 is an exploded view of embodiments of components of the tracheostomy tube assembly 10 that may include features capable of securing the flange 26 and the cannula 12 to the cap 24. As shown, the cap 24 includes a generally cylindrical body 34 having a proximal end 32 and a distal end 36. The proximal end 32 includes aperture 30 that extends throughout the body 34 and terminates in an aperture (not shown in FIG. 2) provided at the distal end 36 of the body 34. Such apertures are suitable for enabling a free flow of fluids, such as air, throughout the length of the cap 24 when assembled with the flange 26 and the cannula 12 during use in a patient. Further, the cap 24 includes one or more features (not shown in FIG. 2) provided in an interior wall of the aperture extending throughout the body 34 and being adapted to engage portions of the flange 26 and the cannula 12 when assembled, as described in greater detail below. Still further, the diameter of the cylindrical body 34 and the diameter of the aperture 30 of the cap 24 may be dimensioned to accommodate various sized connectors associated with suitable auxiliary equipment as desired for the given application.

In the illustrated embodiment, the flange 26 includes features complementary to those of the cap 24 and the cannula 12 that enable securement of such components together when assembled. For example, the illustrated flange 26 includes an annular ridge 38 that is configured to receive the distal end 36 of the cap 24 about the circumference of the ridge portion of the flange 26. For further example, the flange 26 also includes outer annular protrusions 40 that may be configured to engage with an inner surface of the cap 24 to form an interference fit and a seal between the flange 26 and the cap 24. Still further, the flange 26 also includes inner annular protrusions 42 configured to facilitate the secure attachment of the flange 26 to the proximal end 14 of the cannula 12.

The cannula 12 of the illustrated embodiment includes a curved portion 44 that extends from the proximal end 14 to the distal end 16 and may enable the tube assembly to conform to the patient's anatomy when inserted into the patient's trachea. The cannula 12 also includes a flared portion 46 at the proximal end 14, which may facilitate the attachment of the cannula 12 to one or both of the cap 24 and the flange 26 when assembled. It should be noted, however, that in other embodiments, the cannula 12 may not include a flared portion or the flared portion may be formed during the assembly of the components into a single assembly.

As appreciated by one skilled in the art, the cap 24, the flange 26, and the cannula 12 may be formed from various suitable materials via any appropriate manufacturing process. For example, the cannula 12 may be formed from a soft polyvinyl chloride (PVC) or another suitable plastic (e.g., polyurethane, thermoplastic elastomers, etc.) through an extrusion process. Such materials may enable a desirable contact fit between the cannula 12 and the cap 24 and/or the flange 26. Further, in certain embodiments, the flange 26 may be made of a soft PVC molding, which may provide for increased patient comfort when the flange 26 rests against the patient's neck during use. In some embodiments, the cap 24 may be made of a harder material than the flange 26 and the cannula 12, such as a hard polyvinylchloride, a polycarbonate plastic, or any other suitable material or combination of materials. For example, in one embodiment, the cap 24 may be made of ABS, thus providing rigidity to the cap 24, which may provide a rigid surface for binding of the cannula 12 and the flange 26 as well as for connecting the assembly to one or more auxiliary devices (e.g., a connector associated with a ventilator).

Figure 3:
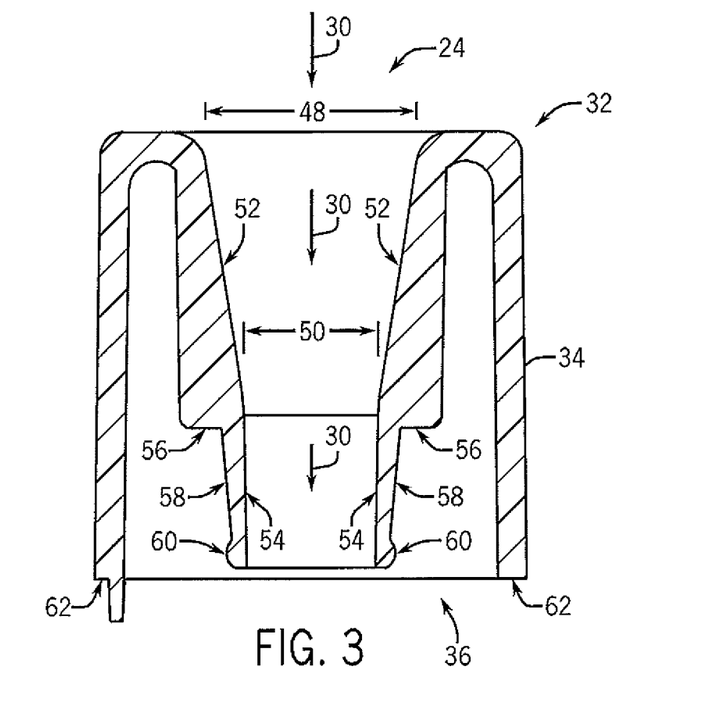
FIG. 3 is a sectional view of the cap of the embodiment of FIG. 1 showing features of the cap in more detail.

FIG. 3 is a sectional view of the cap 24 illustrating a variety of retention features disposed therein and configured to facilitate the coupling of the cap 24 to the flange 26 and the cannula 12. As shown, the cap 24 includes the body 34 through which air passageway 30 extends from the top end 32 of the cap 24 to the distal end 36 of the cap 24. As before, the passageway 30 enables the free flow of fluids, such as air, lengthwise throughout the body 34 of the cap 24. Along the length of the passageway 30, the diameter of the passageway 30 tapers from the top end 32 toward the bottom end 36 of the body 34. That is, a diameter 48 of the top portion of the passageway 30 is greater than a second diameter 50 of the bottom portion of the passageway 30 to form an inner tapered section 52 of the passageway 30. The inner tapered section 52 terminates in an inner uniform section 54 of substantially uniform diameter approximately equal to diameter 50.

The cap 24 also includes inner surfaces 56 that are configured to engage a top portion of the cannula 12 during assembly as described in great detail below. The cap 24 further includes outer tapered surfaces 58 terminating in protrusions 60. The outer tapered surfaces 58 and the protrusions 60 may be dimensioned to receive and retain the flared portion of the cannula 12 when a top portion of the flared end of the cannula 12 is seated against inner surfaces 56. As such, the surface 56, the tapered surface 58, and the protrusions 60 may form a nipple portion of the cap body configured to be received by the proximal end of the cannula such that the nipple portion of the cap is retained in the inner diameter of the cannula. Still further, portions 62, which extend annularly about the bottom portion 36 of the body 34, may be sized and shaped to seat in a complementary ridge located on the flange 26 to facilitate assembly.

Figure 4:
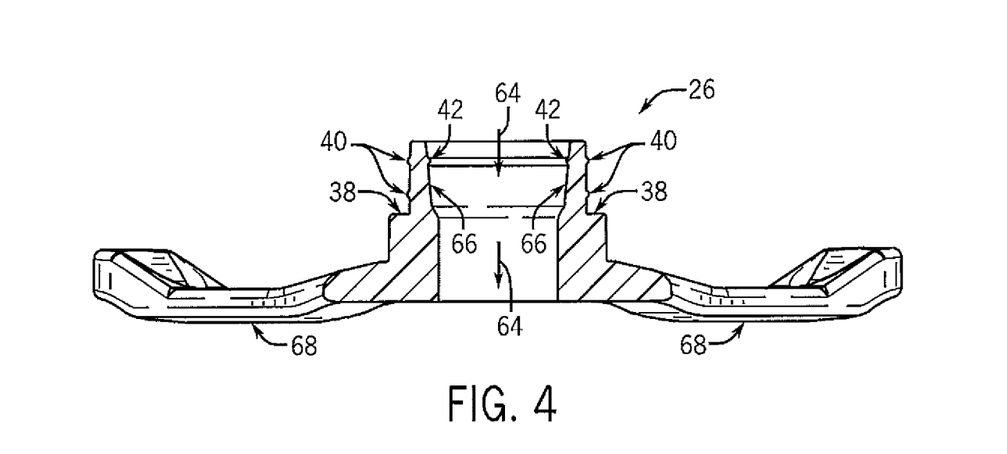
FIG. 4 is a sectional view of the flange of the embodiment of FIG. 1 showing features of the flange in more detail.

FIG. 4 is a sectional view of an embodiment of the flange 26 illustrating features that may facilitate engagement of the flange 26 with the cannula 12 and the cap 24 during assembly. Similar to the passageway 30 of the cap 24, the flange 26 also includes a passageway 64 that is configured to couple to the passageway 30 of the cap 24 and the cannula 12 to enable the airflow to and from the patient during assembly. The flange 26 also includes inner annular protrusion 42 that may engage the flared portion of the cannula 12 in some embodiments to create an interference fit and/or a suitable seal between an inner tapered surface 66 of the passageway 64 and an outer surface of the flared portion of the cannula 12 during assembly. To that end, the inner tapered surface 66 may be dimensioned to complement portions of the flared end of the desired cannula 12 in some embodiments.

Figure 5:
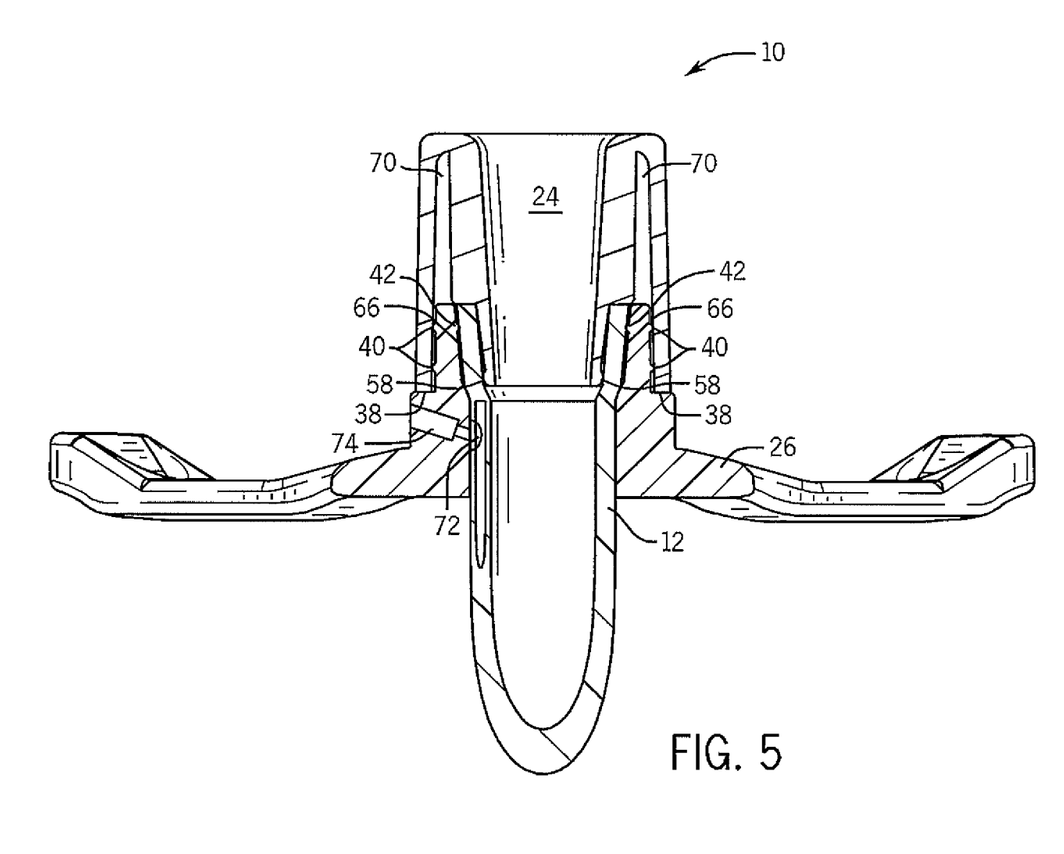
FIG. 5 is a sectional view of the tracheostomy tube assembly of FIG. 1 illustrating internal features of the cap, the flange, and the cannula when the three are joined in the integral assembly.

Further, the flange 26 also includes outer annular protrusions 40 that may facilitate an interference fit and/or a suitable seal between the outer surface of the flange 26 and an inner surface of the cap 24 during assembly, as shown in more detail in the embodiment of FIG. 5. Additional features, such as annular ridge 38, may facilitate coupling of the cap 24 to the flange 26 in the integrated assembly. When assembled and in use, surfaces 68 of the flange 26 may be configured to rest against the patient's neck to secure the assembly to the patient. As such, additional features of the flange 26, such as the flexibility or softness of the material from which the flange 26 is formed, may increase patient comfort.

FIG. 5 is a cross sectional view of the assembled tracheostomy tube assembly 10 illustrating assembly of the three components to form an integral unit. As shown, during assembly, the flared portion 46 of the cannula 12 is lodged between the inner surface 66 of the flange 26 and the inner surface 58 of the cap 24. The flared portion 46 of the cannula 12 may be coupled to the inner surface 58 of the cap 24, for example, via any suitable bonding agent, and to the inner surface 66 of the flange 26, for example, via a solvent bond. Again, features of the flange 26, such as annular protrusion 42, and features of the cap 24, such as surface 58 and annular protrusion 60 may facilitate the lodging of the cannula 12 between portions of the cap 24 and portions of the flange 26.

During assembly, portions of the flange 26 are retained between portions of the cap 24 and the flared portion 46 of the cannula 12. As previously mentioned, annular protrusion 42 facilitates the mating of the flange 26 and the flared portion 46 of the cannula 12. Similarly, annular protrusions 40 facilitate the retention of the flange 26 within the cap 24 when the body 34 of the cap 24 is in contact with the annular ridge 38. As appreciated by one skilled in the art, the connection between the flange 26 and the cap 24 may be secured via any suitable method, such as by the application of a suitable adhesive (e.g., cyanoacrylate adhesive) or through the use of a solvent bond, which may enable the expansion of the annular protrusions 40 to create an appropriate seal.

During assembly, a substantially sealed internal cavity 70 is formed within the cap 24. The internal cavity 70 may be filled with air during use and, due to the substantially airtight seals between the flange 26, the cannula 12, and the cap 24, in certain embodiments, substances (e.g., bodily secretions) may be substantially prevented from entering the sealed cavity 70. Still further, in the illustrated embodiment, the cannula 12 includes a notch 72 that may terminate in a lumen disposed in a wall of the cannula 12, for example, to allow inflation of a cuff disposed near the distal end 16 of the cannula 12. To that end, the illustrated flange 26 includes an opening 74 dimensioned to facilitate connection of the notch 72 to an externally located inflation device.

Figure 6:
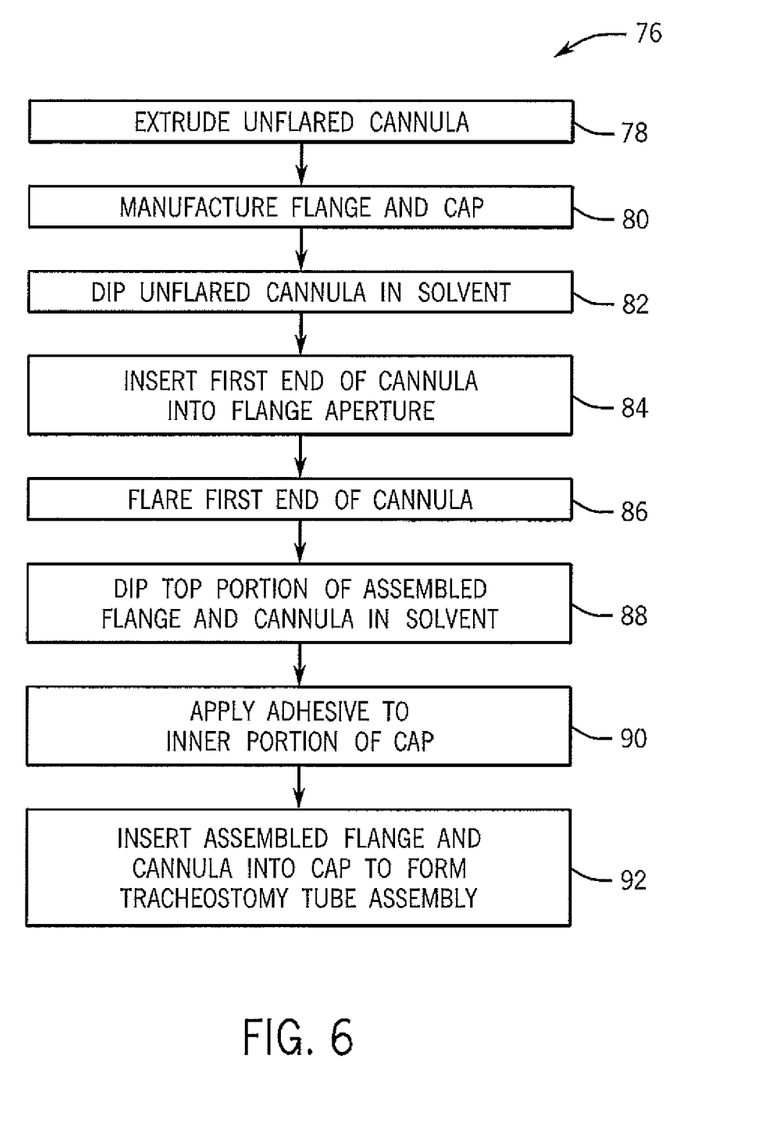
FIG. 6 illustrates steps in an exemplary method that may be utilized to form the exemplary tracheostomy tube assembly of FIG. 1.
Figure 7:
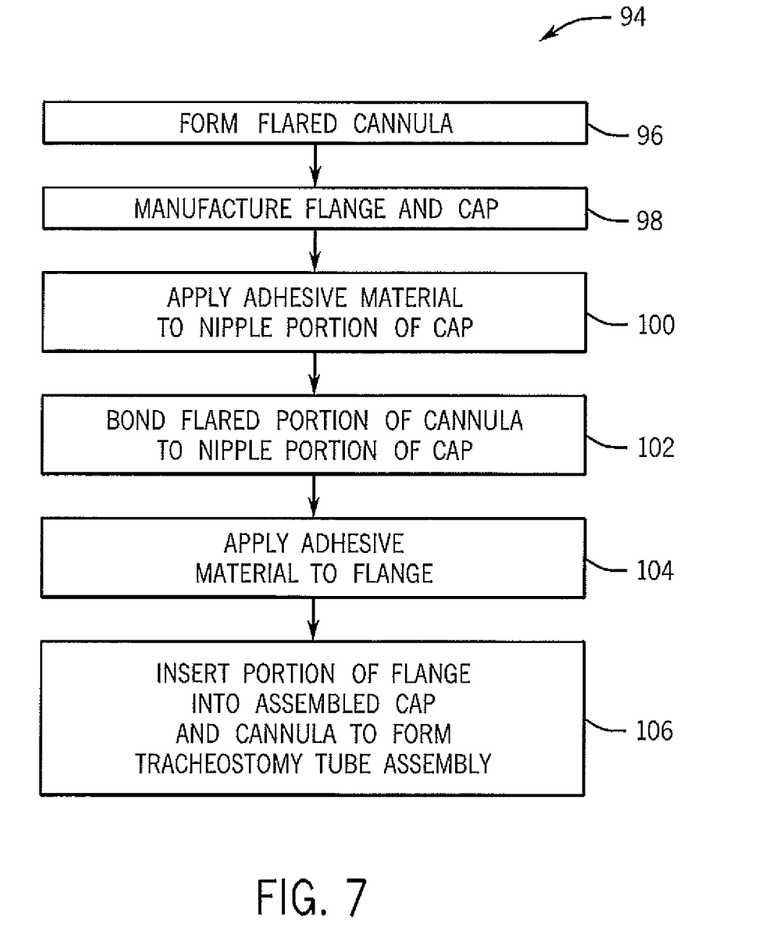
FIG. 7 illustrates an embodiment of an alternate method that may be utilized to form the exemplary tracheostomy tube assembly of FIG. 1.

As appreciated by one skilled in the art, the flange 26, the cannula 12, and the cap 24 may be formed and assembled through various suitable processes. As such, in some embodiments, the components may be coupled together during manufacturing such that the utilized adhesives and bonding processes do not necessitate the use of backfilling, for example, with PVC. In other embodiments, backfilling portions of the assembly with a suitable material may be desirable as determined by the desired manufacturing and assembly methods. FIGS. 6 and 7 illustrate embodiments of presently contemplated methods of assembling and manufacturing the illustrated tracheostomy tube assemblies. However, one skilled in the art may employ any of a variety of suitable processes to form and assemble the devices described herein.

Turning now to the method 76 illustrated in FIG. 6, the method 76 includes the steps of extruding an unflared cannula (block 78) and manufacturing the flange and cap from the desired materials (block 80). The method 76 further includes dipping the unflared cannula in a suitable solvent (block 82) and inserting the first end of the cannula into the flange aperture (block 84). That is, in this embodiment, the cannula and the flange are first coupled to one another. After insertion of the cannula into the flange, the inserted end of the cannula is flared (block 86), and the top portion of the assembled flange and cannula is dipped in solvent (block 88). Finally, a suitable adhesive is applied to the inner portion of the cap (block 90), and the assembled flange and cannula is inserted into the cap (block 92) to form the tracheostomy tube assembly illustrated in FIG. 5.

Alternatively, the method 94 illustrated in FIG. 7 calls for forming of a flared cannula (block 96) and manufacturing of the flange and cap (block 98) before first coupling the flange and the cap. To that end, after forming the components, adhesive is applied to the nipple portion of the cap (block 100), and the pre-flared portion of the cannula is bonded to the nipple portion of the cap (block 102). Once the cannula and the cap are coupled, adhesive material is applied to the flange (block 104), and the flange is inserted into the assembled cap and cannula to form the tracheostomy tube assembly of FIG. 5. Again, such manufacturing and assembly methods are merely presently contemplated embodiments, and one skilled in the art may employ any of a variety of suitable methods to form the illustrated assemblies.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheostomy tube assembly, comprising:
a cannula comprising a distal end and a proximal end, the distal end being adapted to be inserted into a patient's trachea;
an annular cap comprising an annular body having a first surface configured to be received into the proximal end of the cannula; and
a flange member configured to support the tracheostomy tube assembly via engagement with the patient's neck to maintain the flange member outside of the patient's trachea when the distal end of the cannula is inserted into the patient's trachea, wherein the flange member, the annular cap, and the cannula form an integral assembly that remains assembled during intubation, and wherein during intubation, a second surface of the flange member is engaged with the proximal end of the cannula to retain the proximal end between the second surface of the flange member and the first surface of the annular cap, and a third surface of the flange member engages an inner surface of the annular body of the annular cap to retain the flange member between the annular cap and the proximal end of the cannula wherein the inner surface of the annular body and the flange member are bonded to one another.

2. The tracheostomy tube assembly of claim 1, wherein the first surface comprises an annular protrusion configured to facilitate the retention of a portion of the cap in the proximal end of the cannula.

3. The tracheostomy tube assembly of claim 1, wherein the proximal end of the cannula is flared and the first surface of the cap is tapered to complement the flared end of the cannula.

4. The tracheostomy tube assembly of claim 1, wherein the second surface comprises an annular protrusion configured to create an interference fit between the flange member and the proximal end of the cannula.

5. The tracheostomy tube assembly of claim 1, wherein the third surface of the flange member comprises one or more annular protrusions configured to create an interference fit between the inner surface of the annular body and the flange member.

6. The tracheostomy tube assembly of claim 1, wherein the inner surface of the annular body and the flange member are coupled with an adhesive material.

7. The tracheostomy tube assembly of claim 1, wherein the proximal end of the cannula and the second surface of the flange member are solvent bonded.

8. The tracheostomy tube assembly of claim 1, wherein the cap is made of a hard thermoplastic material.

9. The tracheostomy tube assembly of claim 8, wherein the cap is made of acrylonitrile butadiene styrene.

10. A method of forming a tracheal tube assembly, comprising:
assembling a cap to a cannula, the cap comprising an outer wall and a nipple portion together defining an internal cavity, the nipple portion of the cap contacting an inner diameter of a proximal end of the cannula; and
assembling an integral unit that remains assembled during intubation of a patient by assembling a flange to the assembled cap and cannula with a portion of the flange contacting the internal cavity of the cap between the outer wall and the proximal end of the cannula, the flange being configured to support the tracheal tube assembly via engagement with the patient's neck to maintain the flange outside of the patient's trachea when a distal end of the cannula by bonding the proximal end of the cannula to a surface of the flange member is inserted into the patient's trachea.

11. The method of claim 10, further comprising securing the nipple portion of the cap to the proximal end of the cannula by solvent bonding.

12. The method of claim 10, further comprising securing the flange to the outer wall of the cap by applying an adhesive material to the flange.

13. The method of claim 10, further comprising securing the proximal end of the cannula to the flange via solvent bonding.

14. The method of claim 10, wherein the cap is formed from a rigid thermoplastic material.

15. The method of claim 10, wherein the proximal end of the cannula is flared such that the diameter of the proximal end increases along the length of the cannula.

16. A tracheostomy tube assembly, comprising:
a cannula comprising a distal end and a proximal end, the distal end being adapted to be inserted into a patient's trachea;
a cap comprising an outer wall and a nipple portion together defining an internal cavity configured to be received by the proximal end of the cannula, wherein the cannula is configured to be coupled to the cap such that the nipple portion of the cap contacts in an inner diameter of the cannula; and
a flange configured to support the tracheostomy tube assembly via engagement with the patient's neck to maintain the flange outside of the patient's trachea when the distal end of the cannula is inserted into the patient's trachea and comprising an insert portion configured to be retained in the internal cavity of the cap between the outer wall and the proximal end of the cannula, wherein the cannula, the cap, and the flange form an integral unit that remains assembled during intubation of the patient wherein the proximal end of the cannula and a surface of the flange member are bonded to one another.

17. The tracheostomy assembly of claim 16, wherein the proximal end of the cannula is flared and the nipple portion of the cap is tapered to complement the flared end of the cannula.

18. The tracheostomy assembly of claim 16, wherein the nipple portion of the cap comprises an annular protrusion configured to create an interference fit between the nipple portion of the cap and the proximal end of the cannula.

19. The tracheostomy assembly of claim 16, wherein the insert portion of the flange comprises one or more annular protrusions configured to create an interference fit between the outer wall of the cap and the insert portion of the flange.

20. The tracheostomy assembly of claim 16, wherein the cap is made of acrylonitrile butadiene styrene.

* * * * *